United States Patent [19]
Fanger et al.

[11] Patent Number: 5,897,861
[45] Date of Patent: Apr. 27, 1999

[54] BISPECIFIC REAGENTS FOR AIDS THERAPY

[75] Inventors: Michael W. Fanger, Lebanon; Paul M. Guyre, Hanover; Nathan B. Dinces, Canaan, all of N.H.

[73] Assignee: Medarex, Inc., Annandale, N.J.

[21] Appl. No.: 08/243,070

[22] Filed: May 16, 1994

Related U.S. Application Data

[63] Continuation of application No. 07/769,946, Sep. 30, 1991, abandoned, which is a continuation-in-part of application No. 07/373,905, Jun. 29, 1989, abandoned.

[51] Int. Cl.$^6$ .......................... C07K 16/10; C07K 16/28; A61K 39/395; A61K 39/21
[52] U.S. Cl. .................... 424/136.1; 424/143.1; 424/148.1; 530/387.3; 530/388.22; 530/388.35
[58] Field of Search .............................. 424/136.1, 144.1, 424/145.1, 148.1, 153.1, 143.1; 435/69.3, 69.7; 530/388.22, 388.35, 388.7, 391.1, 402, 403, 866, 387.3

[56] References Cited

U.S. PATENT DOCUMENTS

| | | | |
|---|---|---|---|
| 4,444,878 | 4/1984 | Paulus | 435/7 |
| 4,671,958 | 6/1987 | Rodwell et al. | 424/85 |
| 4,676,980 | 6/1987 | Segal et al. | 424/85 |
| 4,816,567 | 3/1989 | Cabilly et al. | 530/387 |
| 4,954,617 | 9/1990 | Fanger et al. | 530/387 |
| 5,013,548 | 5/1991 | Haynes et al. | 424/89 |
| 5,104,790 | 4/1992 | Flesher et al. | 435/5 |
| 5,166,050 | 11/1992 | Shriver et al. | 435/5 |
| 5,169,939 | 12/1992 | Gefter et al. | 530/387.3 |
| 5,180,660 | 1/1993 | Ohno | 435/5 |
| 5,217,895 | 6/1993 | Ohno | 435/240.27 |
| 5,219,728 | 6/1993 | Khayat et al. | 435/7.2 |
| 5,292,668 | 3/1994 | Paulus | 436/547 |

FOREIGN PATENT DOCUMENTS

| | | |
|---|---|---|
| 0308936 | 3/1989 | European Pat. Off. ..... A61K 39/395 |
| 2 197 322 | 5/1988 | United Kingdom . |
| 2 197 323 | 5/1988 | United Kingdom . |

OTHER PUBLICATIONS

Zarling, J. M. et al., J. Immunol. 140:2609–2613, Lysis of cells infected with HIV–1 by human lyphocytes targeted with monoclonal antibody heteroconjugates, Apr. 15, 1988.
Anasetti, C. et al., J. Immunol. 139:1772–1779, Induction of alcium flux and enhancement of cytolytic activity by natural killer cells by cross–linking of the sheep erythrocyte binding proteins (CD2) and the Fc–receptor (CD16), Sep. 15, 1987.
Fleit, H. B. et al., PNAS 79:3275–3279, Human neutrophil Fc–gamma receptor distribution and structure, May 1982.
Paul, W.F., Fundamental Immunology (1993), pp. 308–309, Raven Press, N.Y.
Traunecker, A. et al. (1989) "High efficient neutralization of HIV with recombinant CD4–immunoglobulin molecules" *Nature* 339:68–70.
International Search Report for EP 96 20 1024.5 issued Aug. 13, 1996.
Anderson et al. (1986) J. Biol. Chem. 261:12856 (preprint enclosed).
Shen et al. (1986) J. Immunol. 137:3378–3382.
Karpovsky et al. (1984) J. Exp. Med. 160:1686–1701.
Till et al. (1988) Science 242:1166–1168.
Chaudhary et al. (1988) Nature 335:369–372.
Capon et al. (1989) Nature 337:525–530.
Clark et al. (1990) in *Bispecific Antibodies and Targeted Cellular Cytotoxicity*, Second International Conference, Seillac, France, pp. 243–247.
de Leij et al. (1990) in *Bispecific Antibodies and Targeted Cellular Cytotoxicity*, Second International Conference, Seillac, France, pp. 249–253.
Nitta et al. (Feb. 17, 1990) *The Lancet*, pp. 368–371.
Ball et al. (1992) *J. Hematotherapy* (in press) pp. 85–94.
Connor et al. (Nov. 1991) *Proc. Natl. Acad. Sci USA*, Vo. 88, pp. 9593–9597.
Mabondzo et al. (1992) *The Journal of Infectious Diseases* 166:93–9.
W. F. Paul, *Fundamental Immunology*, 3rd edition (1993), Raven Press, New York. pp. 1375–1397.
Takeda, A. et al., J. Clin. Invest. 89:1952–1957 (1992), "distinction of human immunodeficiency virus type 1 neutralization and infection enhancement by human monoclonal antibodies to glycoprotein 120".

*Primary Examiner*—Thomas M. Cunningham
*Attorney, Agent, or Firm*—Lahive & Cockfield, LLP; Jane E. Remillard; Giulio A. DeConti, Jr.

[57] ABSTRACT

Bispecific molecules which react both with the high-affinity Fcγ receptor (FcγRI) of effector cells and with the human immunodeficiency virus (HIV), or component thereof are disclosed. Binding of these bispecific molecules to the FcγRI is not blocked by the binding of the Fc region of IgG to that same receptor, as the bispecific molecules are specific for an epitope on the FcγRI distinct from the Fc binding epitope. The bispecific molecules are useful for targeting human effector cells to a target on HIV. Also disclosed are methods of treating HIV infection using these bispecific molecules.

14 Claims, 4 Drawing Sheets

BISPECIFIC REAGENTS FOR AIDS THERAPY

CROSS-REFERENCE TO RELATED APPLICATION

This application is a continuation of application Ser. No. 07/769,946, filed on Sep. 30, 1991, now abandoned which is a CIP of Ser. No. 07/737,905 file Jun. 29, 1989, now abandoned.

BACKGROUND OF THE INVENTION

In the absence of an effective vaccine or therapy, the incidence of acquired immune deficiency syndrome (AIDS) in the United States and other countries is likely to increase during the next few years. Preventing infection with the human immunodeficiency virus (HIV) will depend upon education and counselling to prevent transmission among the populations at risk for AIDS.

Recently, the initial events in infection of human T lymphocytes, macrophages, and other cells by HIV have been elucidated These events involve the attachment of the HIV envelope glycoprotein gp120 to its cellular receptor, CD4. Cells that lack CD4 are not susceptible to HIV infection, but become susceptible after they are transfected with the CD4 gene and express CD4 on their surfaces This information has led to studies of the use of recombinant CD4 (rCD4) which might be used therapeutically to block the CD4-binding sites on HIV, preventing it from binding to CD4 on host cells. However, this would provide only a passive blockage of virus infection, and would not lead to active elimination of the virus.

A therapeutic approach has been developed to eliminate the virus. This involves linkage of CD4 to the Fc region of human IgG. Capon et al. *Nature* 337:525 (1989). The Fc region of human IgG is the natural ligand for receptors on monocytic cells. Moreover, in the Fc portion of IgG reside immunoglobulin functions such as Fc receptor binding, protein A binding and complement fixation. These properties of the Fc portion of human immunoglobulin are the major mechanisms for elimination of pathogens. Fc activates the complement pathway, resulting in lysis of the pathogen, whereas binding to the Fc receptors on effector cells can lead to ingestion of the pathogen by phagocytosis or lysis by killer cells.

Nevertheless, the vast amount and diversity of natural antibodies (i.e. non-HIV specific IgG) found in vivo remains a major obstacle to this kind of in vivo therapy since non-HIV specific IgG would be expected to block binding of the Fc region with Fc receptors. A need exists to develop a therapeutic modality that overcomes these problems.

SUMMARY OF THE INVENTION

This invention pertains to bispecific molecules which can bind a pathogen and/or which can simultaneously target the pathogen and pathogen-infected cells for ingestion and destruction by effector cells such as monocytes, macrophages, eosinophils, granulocytes, and neutrophils. The bispecific molecules of this invention have a first binding specificity for a pathogen (e.g. a virus such as HIV) and a second binding specificity for an Fcγ receptor such as the high-affinity Fcγ receptor (FcγRI). The binding specificity for the FcγRI is for an epitope which is distinct from the Fc ligand binding domain for the Fc region of immunoglobulin G (IgG). Thus, the bispecific molecules are capable of binding to IgG-occupied Fcγ receptors on effector cells.

For example, if the target pathogen is a virus such as HIV, the targeted viral component can be the envelope glycoprotein gp120 or gp41 of HIV or a fragment thereof. The binding specificity for gp120 can be provided in several ways. It can be provided by the CD4 molecule of hematopoietic cells or just the CD4 binding domain thereof Alternatively, the gp120 specificity can be provided by a gp120-specific antibody or gp120-binding fragment thereof. The binding specificity for the high affinity Fcγ receptor is provided by an antibody which binds to an epitope of the Fc receptor, the binding of which is not blocked by the binding of human IgG to the Fc receptor, and is thus distinct from the Fc ligand binding site on FcγRI.

The bispecific molecules of this invention can be used alone or they can be pre-bound to effector cells having the appropriate Fc receptor before use. In either form they are administered to a patient in a therapeutic amount sufficient to reduce viral infectivity. These molecules can also be used in conjunction with other molecules. For example, molecules of this invention can be used with cytokines such as interferon-γ which can activate or enhance their therapeutic potential. The effector cells can be obtained from the patient or from other sources so long as the cells are compatible with the immune system of the patient.

The binding of bispecific molecule to the effector cell results in a targeted effector cell, i.e., an effector cell to which is bound a bispecific antibody or heteroantibody containing antigen binding regions specific for a desired pathogen. The targeted effector cells can be used to bring about antibody-dependent cell mediated cytolysis (ADCC) and/or phagocytosis of the target cells in vivo.

BRIEF DESCRIPTION OF THE DRAWINGS

The foregoing and other objects of the present inventions the various features thereof, as well as the invention itself may be more fully understood from the following description, when read together with the accompanying drawings in which.

DETAILED DESCRIPTION OF THE INVENTION

Figure 1:
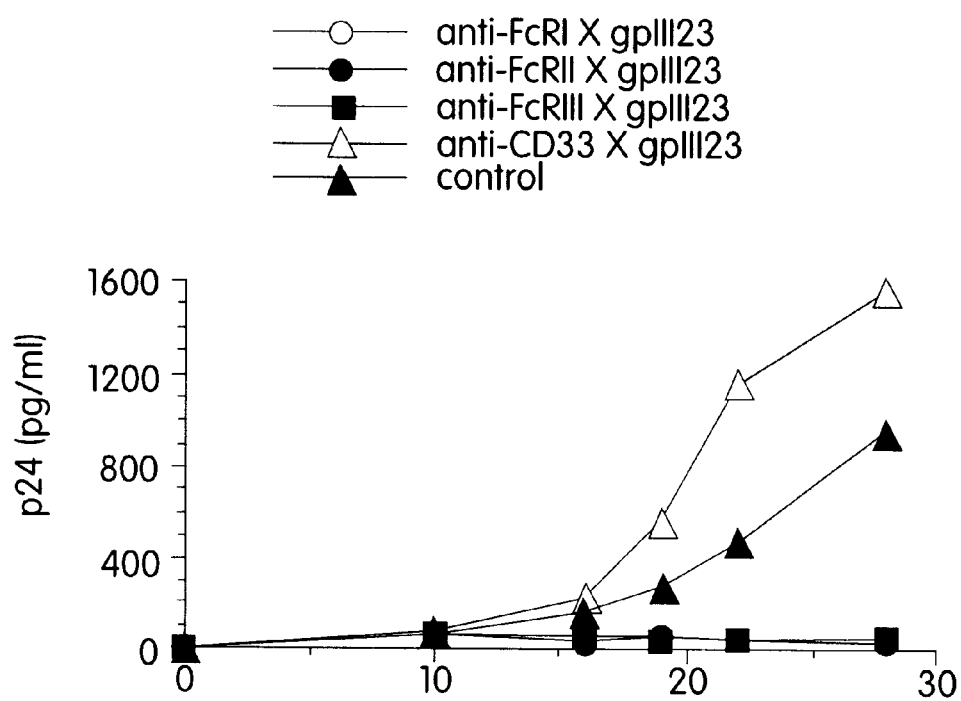
FIG. 1 is a graph delineating the ability of FcγR to inhibit infection of human monocytes. Monocytes were infected with HIV-1IIIB in the presence of anti-FcγR or control bispecific antibody containing Fab gpIII23. Production of HIV-1 from infected cultures was determined by measuring p24 antigen in culture supernatants.

The bispecific molecules of this invention have at least two distinct binding specificities: a binding specificity for a pathogen such as a viral component; and a binding specificity for a Fcγ receptor of effector cells.

The Fc-receptor binding specificity is provided by a binding agent which binds to the high affinity (p72) Fcγ receptor (FcγRI) for human IgG without being blocked by the binding of the receptor to the Fc portion of human IgG. The preferred Fcγreceptor binding agent is an antibody, antibody fragment, antibody variable region, or genetic construct having the following characteristics: (a) it reacts specifically with the high affinity Fey receptor (FcγRI); (b) it reacts with the FcγRI through the antibody's antigen binding region and not its Fc portion; (c) it reacts with an epitope of FcγRI which is distinct from the Fc binding (i.e. ligand binding) site of the receptor; and (d) it binds ligand (erg., Fc)-occupied receptor.

The anti-Fcγ receptor antibodies of this invention can be produced as described in U.S. Pat. No. 4,954,617 (Fanger et al., "Monoclonal Antibodies to Fc Receptors for Immunoglobulin G on Human Mononuclear Phagocytes"), the teachings of which are incorporated by reference herein.

The binding specificity for the pathogen component can be any binding agent specific for an antigen of the pathogen For example, if the targeted pathogen is a virus, viral antigens such as those associated with Epstein Barr virus (EBV glycoprotein: Mackett et al. (1985) *EMBO J.* 4:3229–3234); human Influenza virus (haemagglutinin: Stephens et al. (1986) *EMBO J.* 5:237–245); hepatitis B virus (HBV major surface antigen: Purcell et al. *Am. J. ed. Sci.* 270:395–399 (1975)); and HIV (capsid env glycoproteins: Fauci (1988) *Science,* 239:617–622) can be used as the source of viral target antigen needed to produce the binding specificity for molecules of this invention.

In preferred embodiments for HIV treatment, the HIV component for which the bispecific molecule has affinity are the glycoproteins gp120 and gp41 of HIV, found in the viral envelope and in cells harboring infectious HIV. This affinity can be provided by naturally-occurring or recombinant forms of the CD4 receptor of T cells or by fragments of the CD4 receptor including the HIV-binding domain of CD4. It is well known that CD4, expressed on T-lymphocytes, is the receptor for the HIV envelope glycoprotein gp120. The CD4 protein is also the primary receptor for HIV entry into host cells, and for membrane fusion which contributes to cell-to-cell transmission of HIV and to its cytopathic effects (Maddon et al. *Cell* (1986) 47:333–348). Since the CD4 antigen was identified as the cell-surface receptor for HIV, it has been repeatedly shown in vitro, that soluble forms of CD4 antigen can block the infectivity of the virus (Traunecker et al. (1988) *Nature* 331:84–86). Soluble CD4 inhibits diverse variants of HIV, indicating that all these viruses may share a relatively conserved CD4-binding region Soluble CD4 analogs or CD4 fragments with an affinity for gp120 comparable to that of intact CD4 can be prepared using methods described in the art. See, for example, Berger et al. (1988) *Proc. Natl. Acad. Sci. (USA)* 85:2357–2361; Arthos et al. *Cell* (1989) 57:469–481. Soluble CD4 fragments lack the hydrophobic transmembrane portion or contain only a small fraction of this transmembrane portion. These soluble fragments can be produced enzymatically by cleaving the extracellular portion from the transmembrane portion. Soluble CD4 fragments and CD4 analogs can be also produced recombinantly by inserting truncated CD4-encoding cDNA into expression vectors. CD4 polypeptide can be produced by such cells and the soluble CD4 can be tested for its ability to bind gp120 using standard coimmunoprecipitation assays. See, for example Smith et al. (1987) *Science* 238:1704–1707.

Alternatively, the HIV binding specificity of the molecules of this invention can be provided by anti-gp120 antibodies or gp120-binding fragments thereof These antibodies can also be produced by conventional monoclonal antibody methodology, e.g. the standard somatic cell hybridization technique of Kohler et al. (*Nature* (1975) 256:495), using the gp120 glycoprotein, or fragments thereof, as the immunogen. See, for example, Pasquali et al. (1990) *AIDS Res. Hum. Retrov.* 6:1107–1113; Fung et al. (1987) *Biotechnology* 5:940–946; and Sun et al. (1989) *J. Virol.* 63:3579. In brief, an animal such as a mouse is immunized with gp120 of HIV. The gp120 can be purified, or partially purified from viral lysates for this purpose. The purification of gp120 can be accomplished by affinity chromatography with antibody against gp120. After immunization, B cells are taken from the immunized animal and then fused with an immortalizing cell such as a myeloma cell. See, for example, Fung et al. (1987) *Biotechnol.* 5:940–946. It will be appreciated that subunits of gp160 can also be employed as the HIV component to which a binding specificity is provided. For example, antibodies can be prepared against the gp41 transmembrane protein as well as smaller gene products of the envelope gene of HIV. Sees for examples Robey et al. *Science* (1985) 228:593–595.

Bispecific molecules of this invention can also be prepared by conjugating a gene encoding a binding specificity for a pathogen (i.e. virus or viral antigen such as CD4) to a gene encoding at least the binding region of an antibody chain which recognizes the Fcγ receptor (FcγR). This genetic construct is transfected into a host cell (such as a myeloma) which constitutively expresses the corresponding heavy or light chains thereby enabling the reconstitution of a bispecific, two-chain antibody (or two-chain fragment thereof such as Fab) having a binding specificity for a pathogen and for the FcγR. Such constructs can be used to target viral infectious agents and infected cells through the FcγR. Construction and cloning of such a gene can be performed by standard procedures.

The bispecific molecules of this invention can be of several configurations. Bispecific antibodies resemble single antibodies (or antibody fragments) which have two different antigen binding sites (variable regions) Bispecific antibodies of this invention have one binding site for Fcγ receptor and one binding site for a viral epitope. Bispecific antibodies can be produced by chemical techniques (see e.g., Kranz et al. *Proc. Natl. Acad. Sci. USA* 78:5807 (1981)), by "polydoma" techniques (see U.S. Pat. No. 4,474,893, issued to Reading) or by recombinant DNA techniques Heteroantibodies are two or more antibodies, or antibody binding fragments (Fab) linked together, each antibody or fragment having a different specificity. Bivalent heteroantibodies of this invention comprise an antibody (or fragment) specific for Fcγ receptor, coupled to an antibody (or fragment) specific for a viral epitope. Heteroantibodies can be prepared by conjugating Fcγ receptor antibody with antibody specific for an epitope of the HIV envelope glycoprotein gp120. A variety of coupling or crosslinking agents can be used to conjugate the antibodies Examples are protein A, carboiimide, dimaleimide, dithio-bis-nitrobenzoic acid (DTNB), N-succinimidyl-S acetyl-thioacetate (SATA)e and N-succinimidyl-3-(2-pyridyldithio) propionate (SPDP) SATA and DTNB are the preferred agents; procedures for crosslinking antibodies with these agents are known in the art. See e.g., Karpovsky et al. (1984) *J. Exp. Med.* 160:1686; Liu et al. (1985) *Proc. Natl. Acad. Sci. USA* 82:8648; Segal et al., U.S. Pat. No. 4,676,980 (Jun. 30, 1987); and Brennan *Biotech.* 4:424 (1986).

The bispecific molecules of this invention can also be prepared as recombinant molecules. Constructs can be developed that comprise genes encoding viral receptors linked to genes encoding the binding site (variable region) of anti-FcγR antibody. Thus, a recombinant nucleic acid which encodes a molecule having dual specificity can be prepared by linking a gene encoding a receptor for a viral antigen (e.g. a cell-surface receptor such as CD4 which binds to gp120 on HIV or HIV-infected cells) to the gene encoding either the light or heavy chain variable region of an anti-FcγR antibody. These genetic constructs, or other constructs linking genes for different viral receptors to the anti-FcγR antibody genes can be expressed in suitable host cells.

Bispecific molecules of this invention can be administered to target the killing of virus and/or virally infected cells. The molecules can be given intravenously in free form Alternatively, the molecules can be attached to the surface of effector cells in vitro and the osponized cells can be administered. In each mode the principle is the same; the effector cell is targeted toward the virus.

Effector cells are human leukocytes, preferably macrophages. Other cells can include monocytes, activated neutrophils, and possibly activated natural killer (NK) cells and eosinophils. Monocyte-derived macrophages can be treated with IFN-γ to increase the number of Fc receptors for attachment of the bispecific molecule or heteroantibody. Neutrophils and NK cells can also be activated with IFN-γ in this way. The effector cells may also be activated before targeting by other cytokines such as tumor necrosis factor, lymphotoxin, colony stimulating factor, and interleukin-2. If desired, effector cells for targeting can be obtained from the host to be treated or any other immunologically-compatible donor.

The osponized effector cells can be administered as a suspension of cells in a physiologically acceptable solution. The number of cells administered can be in the order of $10^8$–$10^9$, but will vary depending on the therapeutic purpose. In general, the amount will be sufficient to obtain localization of the effector cell at the target cell or pathogen, and to effect killing of the cell or pathogen by antibody dependent cell-mediated cytolysis (ADCC) and/or phagocytosis. Routes of administration can also vary. The targeted effector cells could be administered intravenously, intramuscularly, or intraperitoneally.

Bispecific molecules of this invention link viral-specific binding agents to FcγR on effector cells in such a way that the large excess of human IgG in vivo does not interfere with binding of the molecule to effector cells or interfere with functioning of effector cells. This is possible because the anti-FcγR component of these molecules binds to FcγR at an epitope outside of its ligand binding domain. Effector cells (i.e. macrophages) targeted in this way can be employed to bring about antibody-dependent cell-mediated killing of HIV or HIV-infected cells.

The bispecific molecules of this invention have a potentially long half-life in vivo. This can result from the interaction of these constructs with FcγR on all monocytes and macrophages where it might remain for long periods of time, much of it out of circulation, but functionally active throughout the body on all cells of the reticuloendothelial system.

Bivalent and multivalent bispecific molecules of this invention can be more sensitive to triggering the killing response than other constructs because of their bivalent nature. This is because internalization of the construct and killing of the targeted infectious agent requires receptor crosslinking. A bivalent or multivalent bispecific complex will initiate cross-linking more efficiently that a monovalent bispecific construct. Furthermore, the binding avidity of a bivalent bispecific construct is likely to be greater than a monovalent bispecific molecule, and therefore be more effective in clearing HIV and HIV-infected cells. This is an important advantage of a bivalent bispecific molecule. A monovalent molecule comprising, for example, the Fc region of IgG complexed with a viral binding specificity (Capon et al. supra) will bind to only one FcγRI molecule since only one of the Fc regions of an antibody can bind to the high-affinity FcγRI receptor. Constructs of this invention having bivalent bispecific or heteroantibody configurations offer an advantage since they can be manipulated to provide greater avidity or triggering capability.

The invention will be further understood from the following, non-limiting examples.

EXAMPLES

I. MATERIALS

A. Effector Cells

Monocytes were purified from normal volunteers essentially as described by Shen et al. (*Clin. Exp. Immunol.* (1986) 65:387–395), herein incorporated by reference.

B. HIV Preparations

HIV-1JRFL (Koyanagi et al. (1987) *Science* 236:819–822) was cultured in fresh, PHA-stimulated peripheral blood mononuclear cells (PBMC). The culture supernatants were titered by end-point dilution to determine the 50% tissue-culture infectious dose ($TCID_{50}$). HIV-1IIIB was obtained from cultures of infected H9 cells and similarly titered by end-point dilution.

C. Preparation of Antibodies and Antibody Fragments

The derivation and properties of the mouse mAb specific to each of the human Fc receptors (FcγR) are as follows: MAb 32.2 (IgG1) recognizes FcγRI (Anderson et al. (1986) *J. Biol. Chem.* 261:12856–12864) U.S. Pat. No. 4,954,617; mAb IV.3 (IgG2b) recognizes FcγRII (Looney et al. (1986) *J. Immunol.* 136:1641–1647; Looney et al. (1986) *J. Exp. Med.* 163:826–836); and mAb 3G8 (IgG1) recognizes FcγRIII (Fleit et al. (1982) *Proc. Natl. Acad. Sci.* (USA) 79:3275–3279). Control antibodies used were the mouse mAb 251 (IgG1) specific for CD33 (Peiper et al (1987) *Leukocyte Typing III, White Cell Differentiation Antigens,* (Ed. A. J. McMichael) Oxford University Press, pp. 622–625), and mAb W6/32 (IgG2a) which recognizes a common epitope of HLA-A, -B and -C.

MAb gpIII23, a mouse IgG1, recognizes an epitope of 22 amino acids (residues 302 to 324) localized in the V3 region of HIV envelope glycoprotein gp120 (Pasquali et al. (1990) *AIDS Res. Human Retroviruses* 6:1107–1113). MAb gpI,11,2, a mouse IgG1 (Pasquali et al. (ibid) recognizes an epitope of 23 amino acids at the N-terminus of gp120, a region that is highly conserved between different isolates of HIV-1.

Most of the IgG antibodies were produced in hollow fiber cartridges (Amicon, Danvers, Mass.), and purified from the harvest using a protein-pak 5PQ DEAE column (Waters Chromatography Division, Millipore, Milford, Mass.) and high performance liquid chromatography (HPLC). The gpI,11,2 and W6/32 antibodies were purified from mouse ascites fluid by HPLC gel filtration chromatography using a Bio-Sil TSK 250 column (Bio-Rad, Richmond, Calif.), followed by chromatography on a Protein A-agarose column (Sigma Chemical Co., St. Louis, Mo.).

The $F(ab')_2$ fragments of each of the IgG1 (32.2, 3G8, 251, gpI,11,2 gpIII23) and IgG2a (W6/32) antibodies were made by pepsin digestion (Parham (1983) *J. Immunol.* 131:2895–2902). $F(ab')_2$ fragments were purified by HPLC gel filtration chromatography using a TSK30000 gel filtration column (TosoHaas, Philadelphia, Pa.). IV.3, a mAb of the IgG2b isotype, was digested to Fab fragments using an immobilized papain kit and a Protein A column for purification (Pierce, Rockford, Ill.).

D. Bispecific Antibody Formation

Fab—Fab BsAb were made by formation of disulfide linkages, using 5, 5'-dithiobis-(2-nitrobenzoic acid) (DTNB) (Sigma Chemical Co.). F(ab')$_2$ fragments of 32.2, 3G8, 251, and W6/32 were digested to Fab' fragments by a 30 minute reduction with 10 mM mercaptoethylamine-HCl (MEA) (Sigma Chemical Co.) at 37° C., under nitrogen. DTNB was then added to a final concentration of 20 mM, and the mixture was incubated under nitrogen for at least 3 hours at 25° C. The Fab-TNB was purified from the mixture using a TSK 3000 column. F(ab')$_2$ fragments of gpIII23 and gpI, 11,2 were reduced to Fab'-SH by a 30 minutes incubation with 10 mM MEA at 37° C. and the Fab' isolated using a G-25 Sephadex column (Pharmacia, Uppsala, Sweden). Equimolar amounts of the appropriate Fab-TNB and Fab'-SH antibodies were then mixed under nitrogen and incubated at 22° C. for 18 hours. The Fab×Fab crosslinked conjugate was purified from the mixture by HPLC gel filtration chromatography using a TSK 3000 column with phosphate buffered saline (pH 7.4) and sterilized by 0.2 µm filtration. The total protein concentration of each conjugate was then determined by BCA assay using a Micro BCA kit (Pierce).

To prepare the gpI,11,2 Fab×IV.3 Fab conjugate, gpI,11,2 F(ab')$_2$ was first reduced to Fab' fragments using MEA, and TNB groups were introduced as described above. IV.3 Fab was treated with N-succinimidyl-S-acetyl-thioacetate (SATA) in the presence of 1 mM EDTA, yielding 2–3 SATA groups per Fab fragment. Excess SATA was removed on a G-25 Sephadex column (Pharmacia). IV.3 Fab SATA was then mixed with a 1.5 molar excess of gpI,11,2 Fab-TNB (1.5 moles TNB per mole of SATA) under nitrogen and incubated at 22° C. for 18 hrs. The Fab—Fab cross-linked conjugate was purified as described above, sterilized by 0.2 µm filtration, and stored at 4° C.

II. METHODS AND RESULTS

A. Reactivity of Bispecific Antibody

ELISA assays were performed as follows to demonstrate binding of the anti-gp120 end of the bispecific antibody Purified recombinant gp120 (American Biotechnologies, Inc., Cambridge, Mass.) was added to individual wells of a 96 well plate at a concentration of 0.2 µg/well in phosphate-buffered saline (PBS). The plate was incubated at 37° C. for 4 hrs and then washed with PBS. BSA (5%) in PBS with 0.05% azide was added to each well (150 µl/well), and the plate incubated for one hr at 37° C. After washing with PBS, 100 µl/well of antibody stocks made up in 1% BSA/PBS/Azide (PBA) at a concentration range from 10 µg/ml to 10 ng/ml were added and the plate was incubated 2 hrs at 37° C. The plate was washed thoroughly in PBS, followed by addition of 75 µl/well of goat anti-mouse Ig conjugated to alkaline phosphatase, diluted 1250 in 1% PBA. Following an overnight incubation at 22° C., the plate was washed thoroughly and developed by the addition of 60 µl/well of 2 mg/ml p-nitrophenyl phosphate disodium (PNPP) (Sigma).

The binding of the effector end (anti-FcγR) of the Bispecific antibody was checked by standard fluorescence-activated cell sorter (FACS) analysis. Human buffy-coat cells (10$^6$) isolated by dextran sedimentation from the peripheral blood of normal donors, were mixed with human IgG (Cohn fraction, final concentration 4 mg/ml) to block FcγR, and Bispecific antibody or control antibody (100 µg/ml to 10 ng/ml). Following a 90 minute incubation at 4° C., cells were washed three times in 0.1% PBA, and goat anti mouse IgG-FITC conjugated (F(ab')$_2$) (Caltag, S. San Francisco, Calif.) was added to each sample. After a second 90 min incubation at 4° C., the cells were washed three times in 0.1% PBA and fixed in 1% paraformaldehyde. The percent of cells positive for antibody-binding and the mean fluorescence intensity (MFI) values were determined for each sample using an Ortho 50H cytofluorograph equipped with a 2150 computer.

As previously reported (Fanger et al. (1989) *Immunol. Today* 10:92–99), FcγRI and FcγRII were highly expressed on monocytes and macrophages, while FcγRIII was expressed at low levels on monocytes and high levels on macrophages. As shown in TABLE 1, indirect immunofluorescent staining indicated that Bispecific antibody containing Fab fragments of 32.2, IV.3 and 3G8 linked to Fab anti-HIV-1 mAb (gpIII23 and gpI,11,12) reacted with monocytes to the same extent as the unconjugated Fab anti-FcγR mAbs, confirming both the specificity and binding capacity of the Bispecific antibody.

TABLE 1

Bispecific Antibody Binding To Monocyte FcγR.

| Receptor | mAB | Fab | % positive cells |  |
|---|---|---|---|---|
|  |  |  | —Fab gpIII23 | —Fab gpII.11.2 |
| FcγRI | 32.2 | 98 | 97 | 96 |
| FcγRII | IV.3 | 98 | 99 | 99 |
| FcγRIII | 3G8 | 20 | 27 | 26 |
| HLA-A, B, C | W6/32 | 100 | 100 | 100 |
| CD33 | 251 | 99 | 99 | 98 |

B. Infectivity Assays

Anti-FcγR-anti-HIV Bispecific antibody (containing Fab fragments of mAbgpIII23) or control Bispecific antibody were incubated for 30 min at 37° C. with 50 TCID$_{50}$ of either HIV-1IIIB or HIV-1JRFL. These preparations were then used to inoculate freshly isolated monocytes. The cells were incubated at 37° C. for 4 hr in the presence of virus and antibodies, washed twice, and cultured in 24-well plates at a density of 1×10$^6$ cells per well. Samples of culture supernatants were taken on day 0, and fresh media was added on day 3 of culture.

HIV-1 production was determined at regular intervals by measuring p24 (core) antigen levels in culture supernatants (Abbott Laboratories, Chicago, Ill.) Control cultures infected with HIV-1IIIB in the absence of Bispecific antibody produced low levels of p24, first detected on day 16 of culture (FIG. 2A). Significant increases in p24 levels occurred only after prolonged culture (22 to 28 days). Monocytes infected in the presence of Bispecific antibody that target HIV-1 to either FcγRI, FcγRII or FcγRIII, showed very little p24 production throughout the culture period. Virus production from monocytes infected in the presence of Fab 251-Fab gpIII23 Bispecific antibody was similar to, or greater than, that seen in control cultures (FIG. 1).

Figure 2:
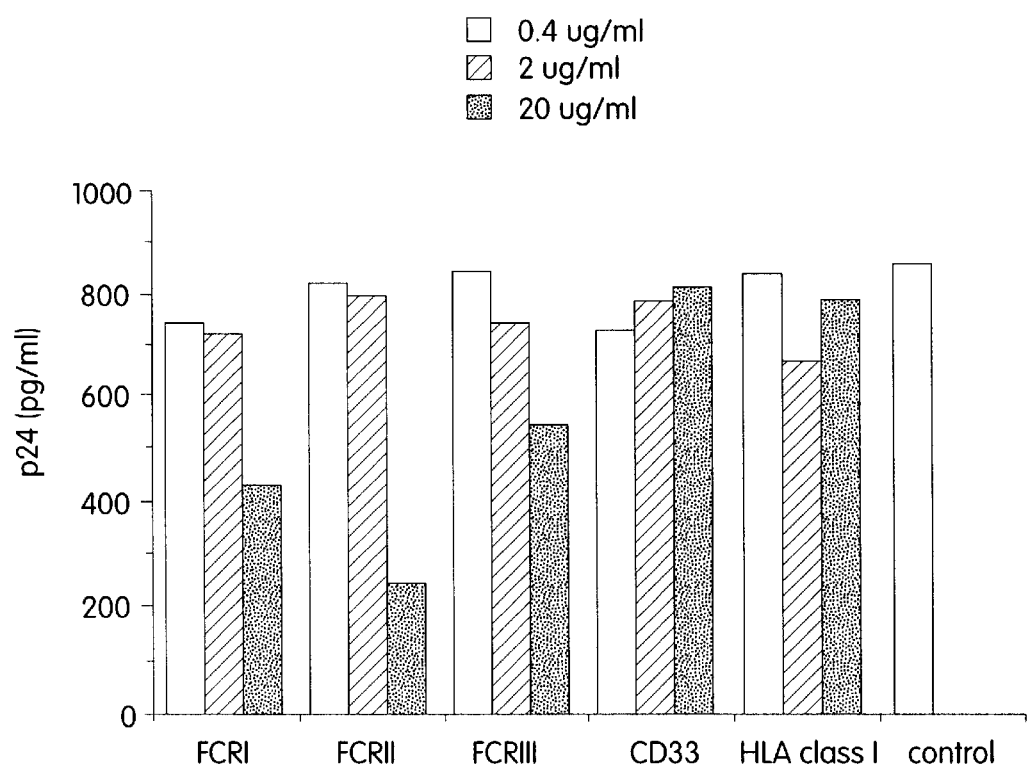
FIGS. 2 is a histogram showing the ability of FcγR to inhibit infection of human monocytes with HIV-1JRFL. Monocytes were infected with HIV-1JRFL in the presence or absence of designated bispecific antibody made using monoclonal antibody gpI,11,2. Virus production in infected cultures was determined by measuring p24 antigen in culture supernatants on day 7 after infection.

That HIV-1 infection of monocytes may be inhibited by interaction of antibody-coated virus with surface FcγR was further examined using the monocytotropic isolate HIV-1JRFL (Koyanagi et al. (1987) *Science* 236,819–822). Bispecific antibody were constructed using Fab fragments of gpI,11,2, which binds a conserved region of gp120, covalently linked to Fab fragments of anti-FcγR or control mAbs. Significant levels of p24 antigen were detected in monocyte cultures infected with HIV-1JRFL in the absence of Bispecific antibody or in the presence of control Bispecific antibody that target the virus to CD33 or HLA-A,B,C, (FIG. 2). In contrasts significantly less p24 was measured in monocyte cultures infected in the presence of Bispecific antibody (20 µg/ml) that target HIV-1 to either FcγRI or to FcγRII. When lower concentrations of anti-FcγR-anti-HIV-1 Bispecific antibody were used (2.0 and 0.4 µg/ml), p24 production was comparable to that seen in control cultures C. FcγRIII-Mediated Infection of Monocytes Peripheral blood monocytes from four different donors were isolated as described above. Monocytes from each donor were infected with HIV-1JRFL in the presence of Fab 3G8×Fab gpI112 which targets HIV-1 to FcγRIII. Bispecific antibody were used at concentrations of 20, 2 and 0.4 µg/ml. Control cultures were infected with HIV-1JRFL in the absence of Bispecific antibody. Levels of p24 antigen in culture supernatants of infected monocytes from each donor were determined on day 7 after infection.

As shown in Table 2, variable decreases in p24 levels were measured in independent experiments using monocytes from different donors following interaction with FcγRIII, and may correlate to the low levels of FcγRIII expressed by peripheral blood monocytes.

TABLE 2

| Donor # | control | [Fab_3G8-Fab gpI11,2] | | |
|---|---|---|---|---|
| | | 0.4 | 2.0 | 20.0 |
| | | p24 (pg/ml) | | |
| 1 | >1000 | 788 | 608 | 446 |
| 2 | >1000 | >1000 | 966 | 712 |
| 3 | 662 | 731 | 656 | 646 |
| 4 | 701 | 832 | 711 | 322 |
| 5 | 810 | 763 | 333 | 154 |

D. Infection of Monocyte-Derived Macrophages

The effect of HIV-I interaction with FcγRI, FcγRII, and FcγRIII on monocyte-derived macrophages was examined since these cells have significant FcγRIII expression (Klaassen et al. (1990) *J. Immunol* 144:599–606)

Freshly isolated monocytes were cultured for 7 days in RPMI 1640 containing 10% FCS, 100 U/ml penicillin, 100 µg/ml streptomycin, and 200 mM 1-glutamine, yielding >99% monocyte-derived macrophages as determined by adherence, histologic staining, and indirect immunofluorescent staining for expression of FcγRI, FcγRII, FcγRIII, and CD4. Anti-FcγR-anti-HIV Bispecific antibody or control Bispecific antibody were incubated for 30 min at 37° C. with 50 TCID$_{50}$ HIV-1JRFL and these preparations were used to inoculate the cells The cells were incubated in the presence of virus for 4 hr at 37° C., washed twice, and then cultured in 24-well plates at $10^6$ cells per well. HIV-1 production was measured on the days shown in FIG. 4.

Figure 3:
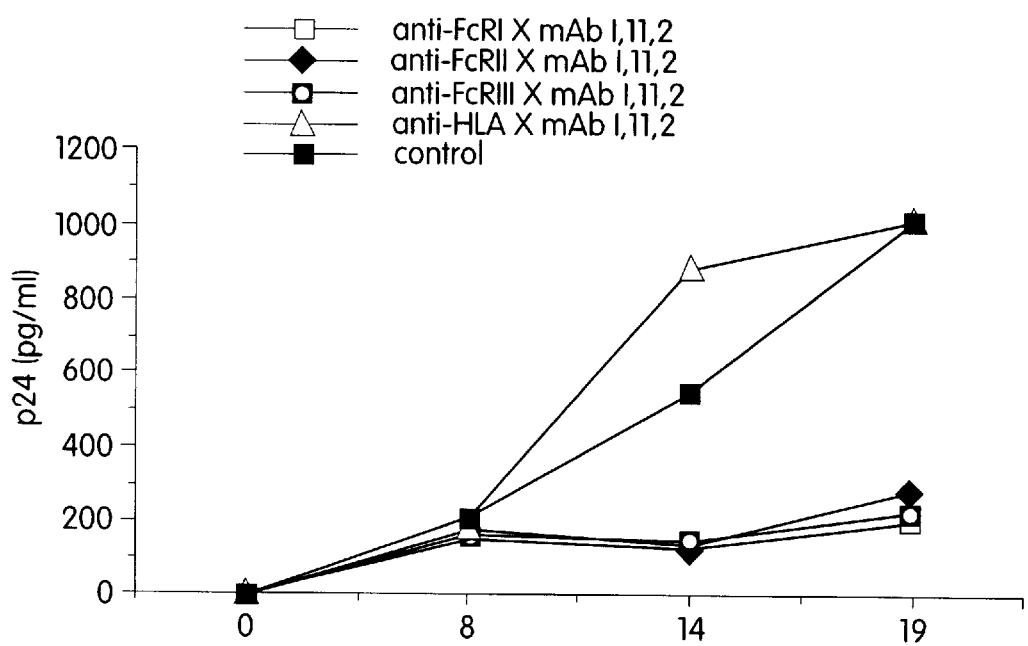
FIG. 3 is a graph showing the ability of FcγR to inhibit infection of monocyte-derived macrophages. Infection of monocyte-derived macrophages was carried out using HIV-1IIIB in the presence of bispecific antibody containing Fab gpI11,2. Control cultures were infected in the absence of bispecific antibody Levels of p24 antigen in the supernatants of infected cultures were determined at the time intervals indicated.
Figure 4:
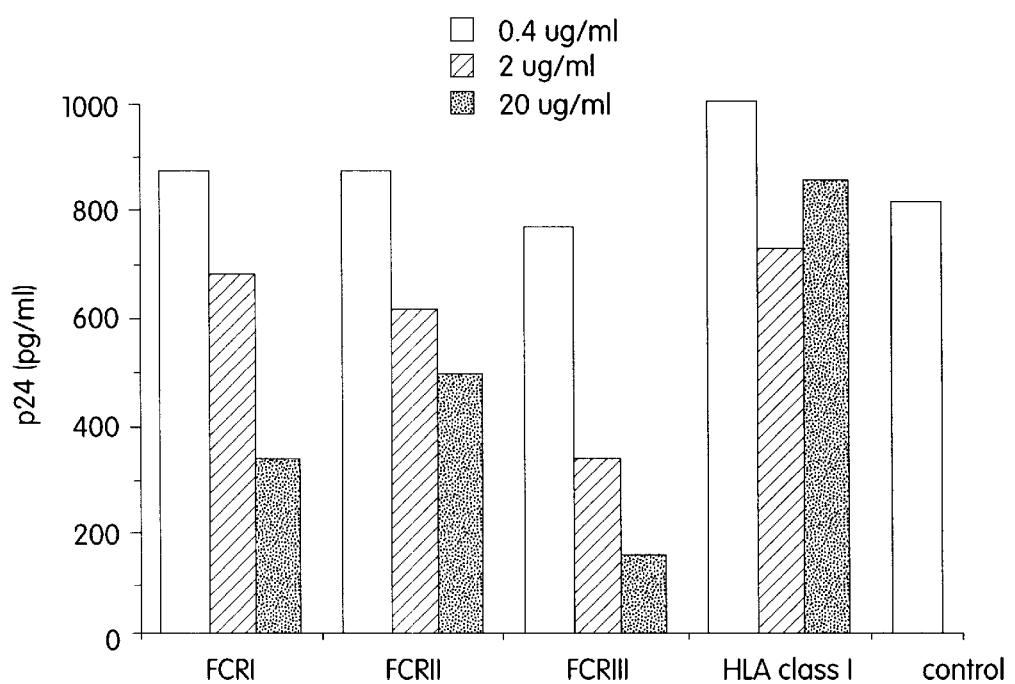
FIG. 4 is a histogram showing infection of monocyte-derived macrophages with HIV-1JRFL in the presence or absence of the designated bispecific antibody used at three different concentrations. Virus production in infected cultures is measured on day 7 after infection.

Virus production from monocyte-derived macrophages infected with HIV-1IIIB occurred from 11 to 14 days after infection, and was observed in control cultures and in cultures infected in the presence of anti-HLA-A,B,C-anti-HIV-1 Bispecific antibody (FIG. 3). Significantly lower levels of p24 were measured in monocyte-derived macrophages cultures infected in the presence of anti-FcγR-anti-HIV-1 Bispecific antibody. Virus production was consistently reduced in monocyte-derived macrophage cultures infected with HIV-1 in the presence of Bispecific antibody that target FcγRIII. This finding was confirmed in similar experiments using the monotropic isolate HIV-1JRFL (FIG. 4).

In summary, virus production was significantly lower in monocyte cultures infected with HIV-1IIIB in the presence of bispecific antibody that target the virus to either FcγRI or FcγRII, when compared to controls cultures infected in the absence of bispecific antibody or in the presence of bispecific antibody that targets the virus to non-FcγR surface antigens (e.g., CD33 or HLA-A, -B, or -C). Interaction of HIV-1JRFL with FcγRI or FcγRII on human monocytes, and FcγRI, FcγRII, or FcγRIII on human monocyte-derived macrophages resulted in significantly lower levels of virus production.

In addition, these findings are directly applicable to antibody-dependent enhancement (ADE) of HIV-1 infections. Unexpectedly, the above results demonstrate that high concentrations of anti-HIV-1 antibody decrease HIV-1 infectivity, in contrast to recent findings in which ADE of HIV-1 infection of FcγR-bearing cells has been demonstrated in the presence of subneutralizing concentrations of HIV-1 antibody-positive sera. See, e.g., Taketa et al. (1988) *Science* 242:580–583; and Homsy et al. (1989) *Science* 244:1357–1360. An explanation is that highly opsonized HIV-1 (treatment with a high concentration of the bispecific molecule of the invention) initiates high affinity, multivalent interactions with FcγR which trigger endocytosis and intracellular degradation of the receptor-virus complex. At lower levels of antibody opsonization there are too few interactions with FcR to initiate FcγR-mediated endocytosis and intracellular degradations but enough to stabilize the virus at the cell surfaces thereby allowing infectivity to proceed through high affinity CD4 interactions Thus, under certain conditions, these results indicate that interaction of antibody-opsonized HIV-1 with FcγR expressed on human macrophages and monocytes reduces viral infectivity through FcγR-mediated cytotoxic mechanisms.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A bispecific molecule comprising:
   (a) a binding specificity for an envelope glycoprotein of the human immunodeficiency virus (HIV) selected from the group consisting of gp120 and gp41, wherein said binding specificity binds to a region that is highly conserved between different isolates of HIV; and
   (b) an antibody, or a fragment thereof, specific for region of an Fcγ receptor of an effector cell, the antibody binding site on the receptor being distinct from the ligand binding site for Fc and binding not being blocked by human IgG.

2. The bispecific molecule of claim 1, wherein said binding specificity comprises and HIV-specific antibody or a fragment thereof.

3. The bispecific molecule of claim 1, which is produced recombinantly.

4. The bispecific molecule of claim 1, wherein said Fcγ receptor is selected from the group consisting of FcγRI and FcγRII.

5. The bispecific molecule of claim 1, wherein the binding specificity for HIV is CD4 or an HIV-binding domain thereof.

6. A bispecific antibody comprising:
   (a) an antibody, or fragment thereof, specific for an envelope glycoprotein of the human immunodeficiency virus (HIV) selected from the group consisting of gp120 and gp41, wherein said antibody or fragment thereof binds to a region that is highly conserved between different isolates of HIV; and (b) an antibody, or a fragment thereof, specific for a region of an Fcγ receptor (FcγR) of an effector cell, the antibody binding site on the receptor being distinct from the ligand binding site for Fc and binding not being blocked by human IgG.

7. The bispecific antibody of claim 6, wherein said FcγR is selected from the group consisting of FcγRI and FcγRII.

8. The bispecific antibody of claim 6, comprising an antibody fragment specific for an envelope glycoprotein selected from the group consisting of gp120 and gp41; and an antibody fragment specific for FcγRI.

9. A method of treating a human immunodeficiency virus (HIV) infection, comprising: administering to a subject a therapeutically effective amount of a bispecific molecule comprising:

(i) at least one binding specificity for an envelope glycoprotein of HIV selected from the group of consisting of gp120 and gp41, wherein said binding specificity binds to a region that is highly conserved between different isolates of HIV; and (ii) an antibody, or fragment thereof, specific for a region of an Fcγ receptor of an effector cell, the antibody binding site on the receptor being distinct from the ligand binding site for Fc and binding not being blocked by human IgG.

10. The method of claim 9, wherein said binding specificity for HIV comprises a gp120-specific antibody or gp120-binding fragment thereof.

11. The method of claim 9, wherein the bispecific molecule is produced recombinantly.

12. The method of claim 9, wherein the effector cell is a human monocyte or macrophage.

13. The method of claim 9, wherein the bispecific molecule comprises an antibody fragment specific for an envelope glycoprotein selected from the group consisting of gp120 and gp41; and an antibody fragment specific for an FCγ receptor.

14. The method of claim 9, wherein the binding specificity for HIV is CD4 or an HIV-binding domain thereof.

* * * * *